United States Patent
Steele

(10) Patent No.: US 9,119,683 B2
(45) Date of Patent: Sep. 1, 2015

(54) INTERSPINOUS IMPLANT WITH OVERLAPPING ARMS

(75) Inventor: Bradley E. Steele, Germantown, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 501 days.

(21) Appl. No.: 13/352,908

(22) Filed: Jan. 18, 2012

(65) Prior Publication Data

US 2013/0184824 A1 Jul. 18, 2013

(51) Int. Cl.
*A61B 17/88* (2006.01)
*A61B 17/70* (2006.01)
*A61F 2/44* (2006.01)

(52) U.S. Cl.
CPC ............... *A61B 17/88* (2013.01); *A61B 17/70* (2013.01); *A61B 17/7047* (2013.01); *A61B 17/7062* (2013.01); *A61B 17/7065* (2013.01); *A61B 17/7068* (2013.01); *A61F 2/44* (2013.01); *A61F 2/4405* (2013.01)

(58) Field of Classification Search
CPC ............... A61B 17/70; A61B 17/7047; A61B 17/7062; A61B 17/065; A61B 17/7068; A61B 17/88; A61F 2/44; A61F 2/4405
USPC .......................... 606/246, 248–249, 277, 279; 623/17.11, 17.14, 17.16
See application file for complete search history.

(56) References Cited

U.S. PATENT DOCUMENTS

| | | | |
|---|---|---|---|
| 7,585,316 B2 | 9/2009 | Trieu | |
| 7,763,073 B2 | 7/2010 | Hawkins et al. | |
| 7,837,688 B2 | 11/2010 | Boyer, II et al. | |
| 8,012,207 B2 | 9/2011 | Kim | |
| 8,070,779 B2 | 12/2011 | Khoo | |
| 8,206,420 B2* | 6/2012 | Patel et al. | 606/249 |
| 8,361,148 B2* | 1/2013 | Malberg et al. | 623/17.11 |
| 2007/0073398 A1* | 3/2007 | Fabian et al. | 623/17.11 |
| 2007/0161992 A1 | 7/2007 | Kwak et al. | |
| 2007/0225724 A1 | 9/2007 | Edmond | |
| 2007/0233088 A1 | 10/2007 | Edmond | |
| 2008/0177312 A1 | 7/2008 | Perez-Cruet et al. | |
| 2008/0208345 A1* | 8/2008 | Hurlbert et al. | 623/17.16 |
| 2008/0243187 A1* | 10/2008 | Protopsaltis | 606/250 |
| 2009/0048676 A1* | 2/2009 | Fabian, Jr. | 623/17.16 |
| 2009/0062915 A1 | 3/2009 | Kohm et al. | |
| 2009/0264929 A1 | 10/2009 | Alamin et al. | |
| 2009/0292315 A1 | 11/2009 | Trieu | |
| 2010/0016973 A1* | 1/2010 | de Villiers et al. | 623/17.16 |
| 2010/0121379 A1 | 5/2010 | Edmond | |
| 2010/0131008 A1 | 5/2010 | Overes et al. | |
| 2010/0222816 A1 | 9/2010 | Gabelberger et al. | |
| 2011/0087285 A1 | 4/2011 | Khajavi et al. | |
| 2011/0313458 A1 | 12/2011 | Butler et al. | |

* cited by examiner

Primary Examiner — Larry E Waggle, Jr.

(57) ABSTRACT

Spinal implants and methods of inserting the implants into an interspinous space and into engagement with spinous processes. The implants may include first and second arms that are separately inserted into the patient. The arms may be attached together within the patient in an overlapping arrangement and pivotally connected at a joint. The arms may be moved about the joint with first ends of each of the arms on a first side of the joint contacting against opposing lateral sides of a first spinous process and second ends of each of the arms on a second side of the joint contacting against opposing lateral sides of a second spinous process. A securing member may contact against the arms and secure the orientation of the arms.

20 Claims, 12 Drawing Sheets

INTERSPINOUS IMPLANT WITH OVERLAPPING ARMS

BACKGROUND

The present application is directed to implants for insertion between vertebral members and, more particularly, to implants with a pair of arms that are pivotally connected together to contact against the lateral sides of the spinous processes.

Vertebral members typically comprise a vertebral body, pedicles, laminae, and processes. The processes are projections that serve as connection points for the ligaments and tendons, and typically include the articular processes, transverse processes, and the spinous process. Intervertebral discs are located between adjacent vertebral bodies to permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

One manner of correcting the damage involves mounting a spinal implant onto the spinous processes, typically in association with a fixation process such as anterior lumbar interbody fusion (ALIF), posterior lumbar interbody fusion (PLIF), intertransverse lumbar interbody fusion (ILIF), and the like. While there currently exists spinal implants for attachment to the spinous proceses, the implants may not be ideal for some situations. As such, there remains a need for alternative spinal implants and related methods.

SUMMARY

The present application is directed to spinal implants and methods of inserting the implants into a patient. One embodiment of a spinal implant includes a first arm and a second arm positioned across the first arm. A ball joint is positioned along intermediate sections of the arms and is formed by first and second extensions on opposing sides of the first arm positioned respectively in first and second sockets in the other arm. The first and second arms are pivotal about the ball joint between first and second orientations with the first ends of each of the arms and the second ends of each of the arms positioned a greater distance apart in the first orientation than in the second orientation.

The spinal implant may also include a first channel that extends from an outer edge of the first arm to the first socket and a second channel that extends from the outer edge to the second socket. The first channel may have a smaller depth than the first socket and the second channel may have a smaller depth than the second socket. One of the first and second arms may include a gap formed between opposing fingers that extends inward from a first end of the arm to at least the ball joint with the other arm positioned within the gap. Each of the first and second extensions may include rounded shapes. A securing member may extend through an aperture in the first arm and contact against at least one of a plurality of parallel ribs on the second arm. The securing member may be configured to fix the relative positions of the first and second arms. Each of the extensions may include the same shape and size and each of the sockets includes the same shape and size.

Another embodiment of a spinal implant includes an elongated first arm with opposing first and second ends. The first arm includes a first connector between the ends that includes a first extension that extends outward from a first side of the first arm and a second extension that extends outward from an opposing second side of the first arm. The implant includes an elongated second arm with opposing first and second ends. The second arm includes a gap that extends inward from the first end towards the second end and first and second fingers on opposing sides of the gap that each include an inner side that faces into the gap. The second arm also includes a first channel and first socket in the inner side of the first finger and a second channel and second socket in the inner side of the second finger with the sockets having a greater depth into the inner sides than the channels. The first and second extensions of the first arm are positioned in the sockets of the second arm to connect the first and second arms.

In this embodiment, the first and second ends of the first arm may be wider than the gap. Each of the first and second extensions may include a rounded shape and the first and second sockets may include a rounded shape. The first connector may be positioned at a mid-point between the first and second ends of the first arm. A securing member may extend through an aperture in one of the first and second arms and may contact against the other of the first and second arms to secure the first and second arms. Each of the first and second channels may be parallel with the first and second fingers. Each of the first and second channels may include an opening at the gap with the openings facing in a common direction as the first end of the second arm. The second arm may include a first portion with a length that is substantially straight, a second portion at the second end with a length that is substantially straight, and an intermediate transverse portion that extends between the first and second portions. The first and second channels may be positioned at the intermediate transverse portion and face towards the first end of the second arm. At least one of the channels may include a tapered shape with a wider outer edge away from the socket and a narrower inner edge at the socket.

One method of inserting an implant into an interspinous space formed between first and second spinous processes includes inserting from a first lateral side a first arm into the patient with the first arm including first and second ends and an extension positioned between the ends. The method includes positioning the first end of the first arm on a second lateral side of the first spinous process and a second end of the first arm on the first lateral side of the second spinous process. The method includes inserting from the second lateral side a second arm into the patient, the second arm including first and second ends and a socket positioned between the ends. The second arm also includes a channel that leads from an outer edge of the second arm into the socket with the channel having a smaller depth than the socket. The method includes positioning the second arm across the first arm with the first end of the second arm on the first lateral side of the first spinous process and the second end of the second arm on the second lateral side of the second spinous process. The method includes inserting the extension of the first arm into the channel of the second arm. The method includes moving the extension along the channel and into the socket.

The method may also include pivoting the first and second arms about an axis that extends through the extension and the socket and adjusting a distance between the first ends and the second ends of the first and second arms. The method may include inserting the first arm into a gap in the second arm that extends into the second arm from the first end. The method may include inserting a second extension of the first arm into a second channel of the second arm, moving the second extension along the second channel, and positioning the second extension into a second socket in the second arm with the second extension and the second socket positioned along an axis that extends through the extension and the socket. The method may include positioning the extension and the socket in the interspinous space. The method may include that the first arm is inserted into the patient before the second arm.

The various aspects of the various embodiments may be used alone or in any combination, as is desired.

DETAILED DESCRIPTION

The present application is directed to spinal implants and methods of inserting the implant into an interspinous space and into engagement with spinous processes. The implant includes first and second arms that are separately inserted into the patient. The arms are attached together within the patient in an overlapping arrangement and pivotally connected at a joint. The arms may be moved about the joint with first ends of each of the arms on a first side of the joint contacting against opposing lateral sides of a first spinous process and second ends of each of the arms on a second side of the joint contacting against opposing lateral sides of a second spinous process. A securing member contacts against the arms and secures the position of the arms.

Figure 1:
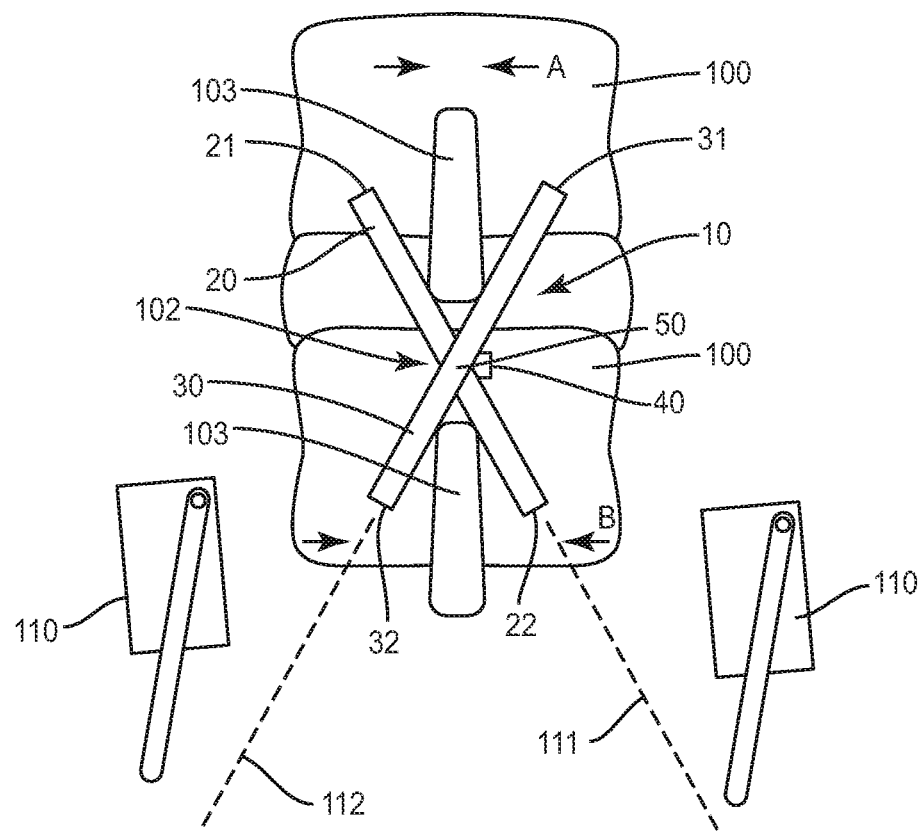
FIG. 1 is a schematic posterior view of a spinal implant inserted into a patient with a pair of insertion instruments.

FIG. 1 schematically illustrates an implant 10 positioned within an interspinous space 102 formed between the spinous processes 103 of two vertebral members 100. The implant 10 includes first and second arms 20, 30 that are attached together in an overlapping arrangement. Each of the arms 20, 30 includes a generally linear shape to facilitate insertion into the patient. The first arm 20 is inserted into the patient from a first lateral direction along insertion path 111. The second arm 30 is inserted from a second lateral direction along the insertion path 112. The arms 20, 30 are moved relative to one another within the patient and connected together to form a joint 50. The insertion paths 111, 112 provide for insertion into the interspinous space 102 without severing the supraspinous ligament that extends along and connects the spinous processes 103. One or more insertion instruments 110 may be used for insertion of the arms 20, 30 into the patient.

The arms 20, 30 may be pivoted about the joint 50 to contact against the lateral sides of the spinous processes 103. First ends 21, 31 of the arms 20, 30 are moved together in the direction indicated by arrows A to contact against the first spinous process 103, and second ends 22, 32 are moved together as indicated by arrows B against the second spinous process 103. Once positioned, a securing member 40 secures the arms 20, 30 in the orientation.

Figure 2:
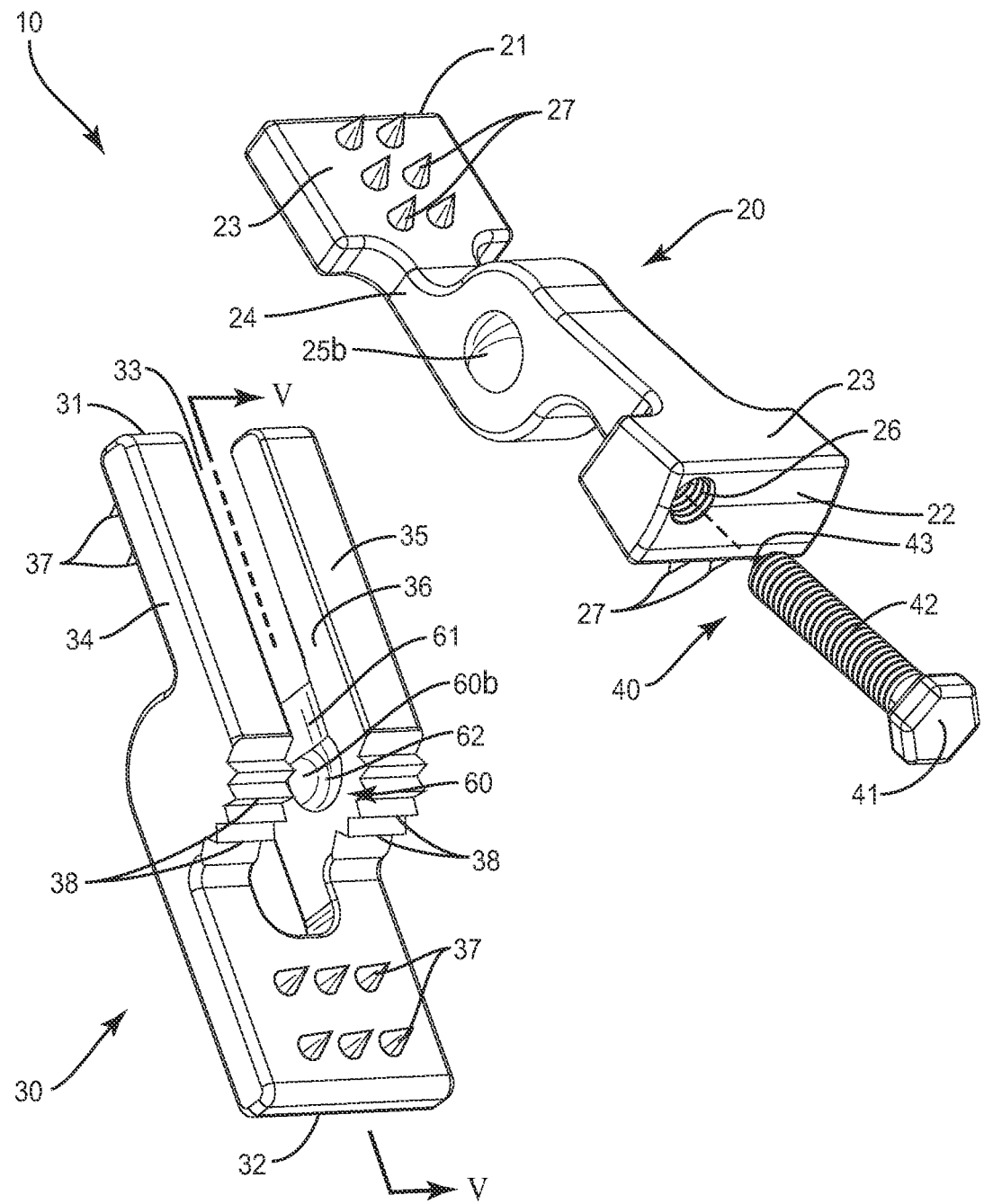
FIG. 2 is an exploded perspective view of an implant.

FIG. 2 illustrates an exploded view of an implant 10 with first and second arms 20, 30 and a securing member 40. The first arm 20 includes an elongated shape with the first end 21 that is initially inserted into the patient and an opposing second end 22. Teeth 27 are positioned in proximity to the ends 21, 22 to engage with the spinous processes 103. One or more teeth 27 are positioned on a first lateral side of the arm 20 at the first end 21, and one or more teeth 27 are positioned on an opposing second lateral side at the second end 22. The teeth 27 may be spaced away from a central section of the arm 20 that is positioned in the interspinous space 102 when the implant 10 is positioned in the patient.

Figure 3:
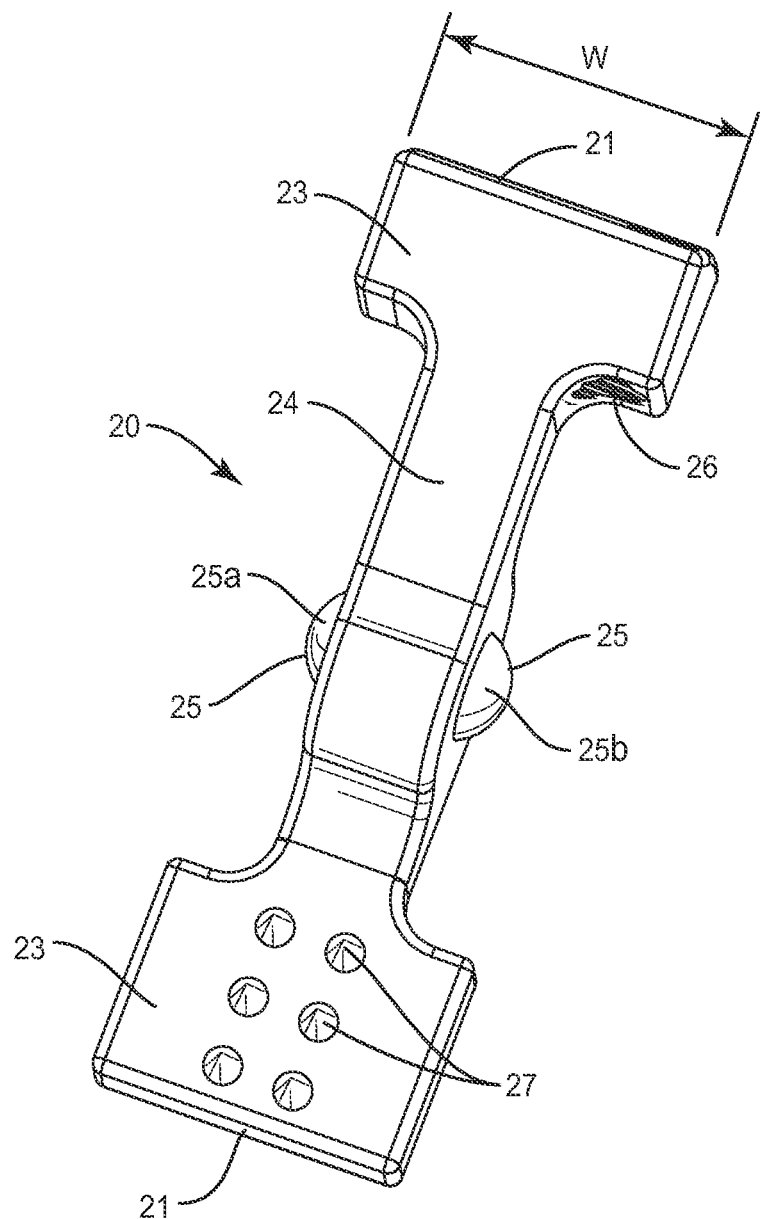
FIG. 3 is a perspective view of a first arm.

As illustrated in FIG. 3, the arm 20 includes enlarged sections 23 at each of the ends 21, 22. These sections 23 include a greater width measured between the anterior and posterior sides of the arm 20 than an intermediate section 24. As illustrated in FIGS. 2 and 3, the teeth 27 may be limited to enlarged sections 23.

A first connector 25 is positioned along the intermediate section 24 and forms the joint 50 that connects the first and second arms 20, 30. In one embodiment as illustrated in FIGS. 2 and 3, the first connector 25 is positioned at a midpoint of the first arm 20 that is half-way between the ends 21, 22. Other embodiments may include the first connector 25 positioned in closer proximity to one of the ends 21, 22.

The first connector 25 may include first and second sections 25a, 25b positioned on opposing sides of the intermediate section 24. Each section 25a, 25b extends outward beyond the side. The sections 25a, 25b may each include a rounded shape that forms a ball joint as will be explained below. In one embodiment, each section 25a, 25b includes the same shape and size, although other embodiments may include differences between the sections 25a, 25b.

The first arm 20 may include a unitary, one-piece construction. Other embodiments may include one or more of the components being separate pieces that are attached together to form the first arm 20.

An aperture 26 extends through the enlarged section 23 at the second end 22. The aperture 24 is configured to receive the securing member 40 to secure the arms 20, 30 in the desired relative position. The aperture 24 may be threaded to engage with the securing member 40.

Figure 4:
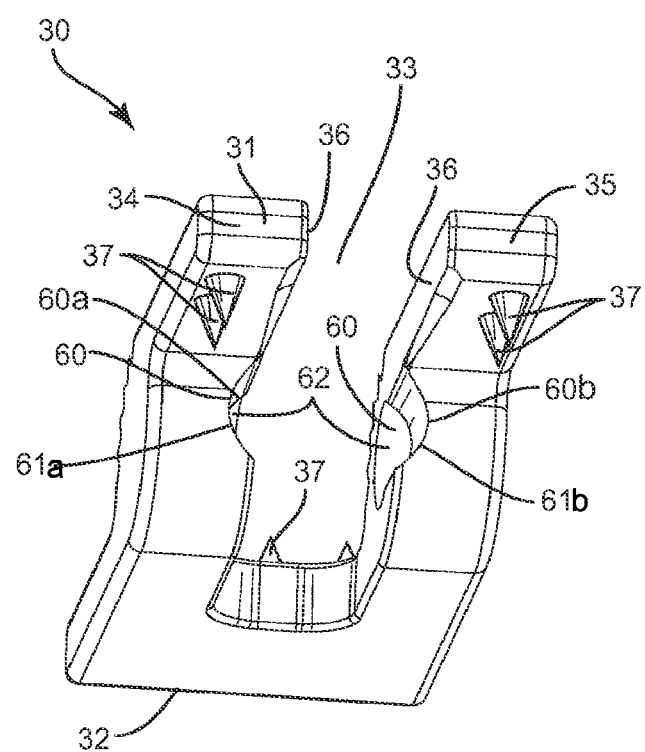
FIG. 4 is a perspective view of a second arm.

The second arm 30 is configured to be separately implanted into the patient and subsequently attached to the first arm 20 within the patient. As illustrated in FIGS. 2 and 4, the second arm 30 includes an elongated shape with a first end 31 that is initially introduced into the patient and an opposing second end 32. Teeth 37 extend outward from a first lateral side at the first end 31 and a second lateral side at the second end 32.

The second arm 30 includes first and second fingers 34, 35 that extend along opposing sides of a gap 33 that extends inward from the first end 31. The fingers 34, 35 include inner surfaces 36 that face towards and define a width of the gap 33. The gap 33 is sized to receive the intermediate section 24 of the first arm 20 when the second arm 30 is inserted into the patient. The length of the gap 33 measured from the first end 31 may vary. The gap 33 terminates short of the second end 32 as the second end 32 includes a continuous shape (i.e., no gap 33). The width of the gap 33 may be consistent along the length, or may vary.

A second connector 60 is located along the arm 30 to form the joint 50 that attaches the first and second arms 20, 30. The second connector 60 is located between the ends 31, 32, with one embodiment being located at a mid-point between the ends 31, 32. Other embodiments may include a location in closer proximity to one of the ends 31, 32.

The second connector 60 includes one or more sections 60a, 60b. FIGS. 2 and 4 include the second connector 60 with a first section 60a formed in the first finger 34 and a second section 60b formed in the second finger 35. Each section 60a, 60b is configured to engage with one of the connector sections 25a, 25b on the first arm 20. Each section 60a, 60b includes a channel 61 that extends inward from an outer edge 63 towards an interior of the second arm 30. A socket 62 is positioned at an end of the channel 61 away from the outer edge.

The channel 61 and socket 62 are shaped to receive the first connector 25. The channel 61 receives the first connector 25 as the first and second arms 20, 30 are moved into engagement. The socket 62 receives the first connector 25 when the arms 20, 30 are connected together. The first connector 25 remains within the socket 62 and forms the joint 50.

Figure 5:
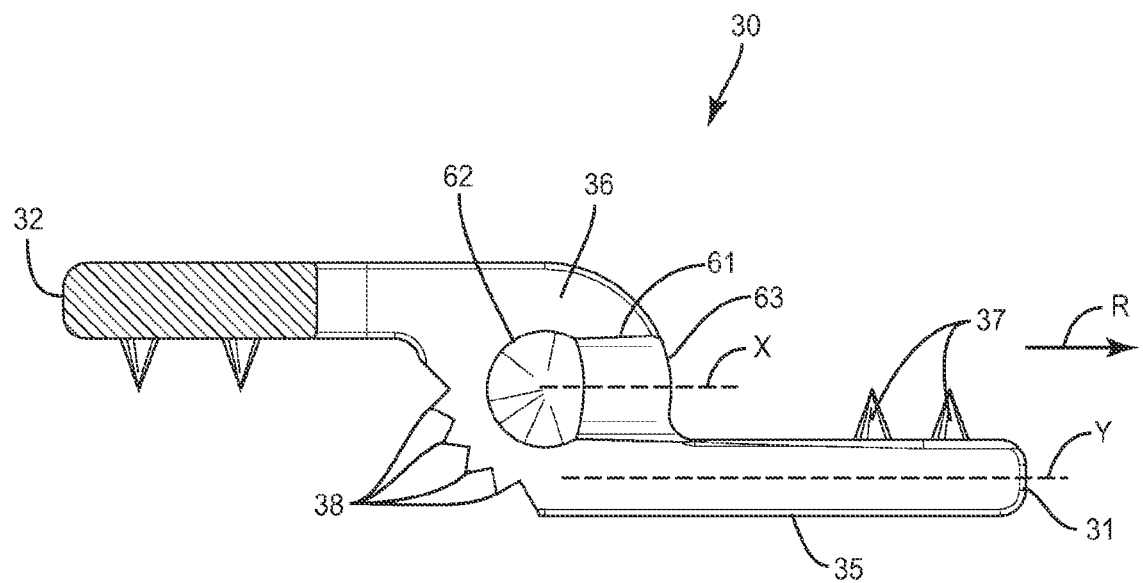
FIG. 5 is a sectional view of the second arm cut along line V-V of FIG. 2.

The shapes of the channel 61 and socket 62 may accommodate the engagement with the first connector 25. In one embodiment as illustrated in FIGS. 2, 4, and 5, the channel 61 includes a rounded shape that matches the rounded shape of the connector 25. Likewise, the socket 62 also includes a rounded shape. The rounded shapes of the connectors 25, 60 form a ball joint that facilitate pivoting movement of the arms 20, 30. The channel 61 and socket 62 may also include different shapes depending upon the shape of the connector 25. The length of the channel 61 measured between the outer edge 63 and the socket 62 may vary. The socket 62 may include a greater depth measured from the inner surface 36 than the channel 61. This greater depth maintains the first connector 25 in the socket 62 and maintains the joint 50.

The channel 61 may be configured to facilitate alignment and engagement with the first connector 25. As illustrated in FIG. 5, the opening into the channel at the outer edge 63 may face in the direction of insertion indicated by arrow R. Further, the centerline line X of the channel 61 may be parallel with the centerline Y of the finger 35. The channel 61 may also be tapered from a wider outer edge 63 to a narrower inner edge at the socket 62. The relatively wider outer edge 63 may facilitate insertion of the connector 25 into the channel 61. The relatively narrower inner edge may provide a smoother transition and the snap fit into the socket 62. In one embodiment, both channels 61 include a tapered shape. Other embodiments may include just one of the channels 61 with a tapered shape.

In embodiments with the second connector 60 including multiple sections, each section (e.g., 60a, 60b) may include the same or different shapes and sizes. FIG. 4 illustrates an embodiment with sections 60a, 60b including the same shape and size.

The second arm 30 further includes a plurality of ribs 38 located to contact with the securing member 40. The ribs 38 may be positioned along an outer edge of the second arm and face towards the second end 22 of the first arm 20 when the arms 20, 30 are connected together. In one embodiment, ribs 38 are positioned along the outer edge of each of the fingers 34, 35.

The implant 10 may also include a securing member 40 for securing the arms 20, 30 in the desired orientation. The securing member 40 may include a head 41 with a shaft 42 that terminates at a tip 43. In one embodiment, the securing member 40 is engaged within the aperture 26 in the first arm 20.

A method of inserting the implant 10 into the patient is illustrated in FIGS. 6-9. An insertion instrument may be used for inserting each of the arms 20, 30 into the patient. In one embodiment, the insertion instrument is a CD HORIZON SEXTANT device available from Medtronic Inc. of Minneapolis, Minn. The arms 20, 30 may be inserted laterally and underneath the supraspinous ligament. This approach prevents damage to this ligament, such as severing the ligament which may be necessary during a posterior approach.

Figure 6:
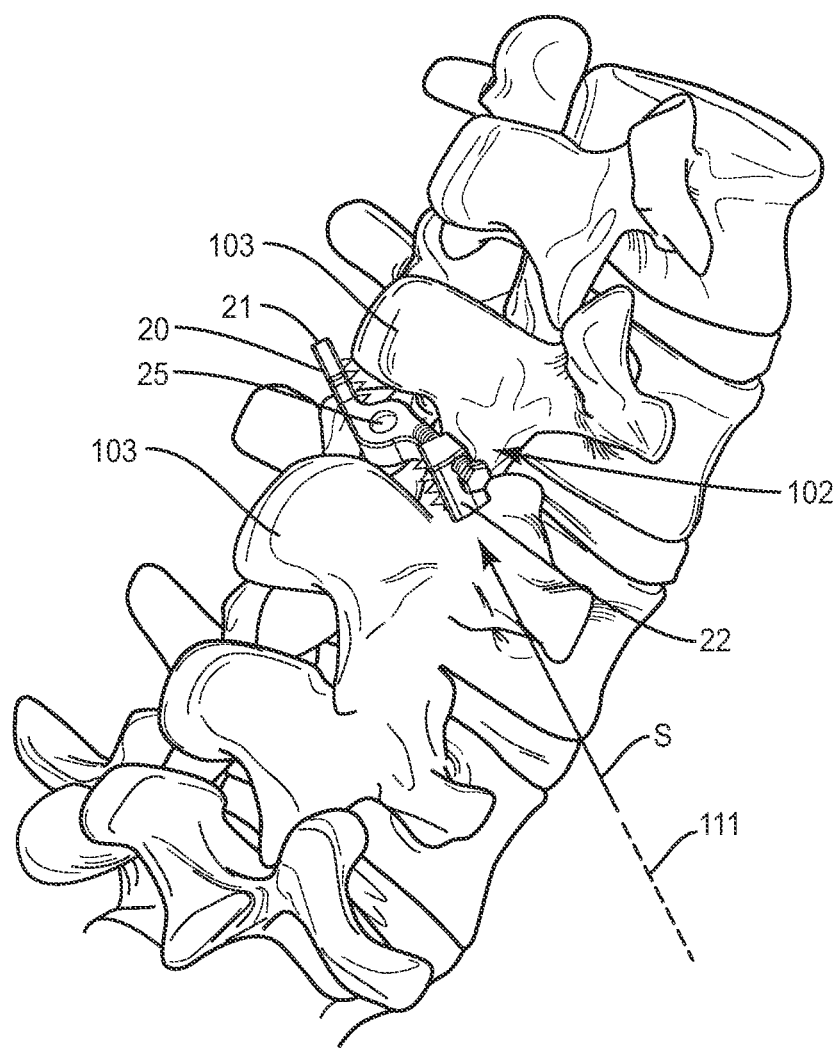
FIGS. 6-9 are perspective views of a method of inserting an implant into a patient and engaging the implant with the spinous processes.

FIG. 6 illustrates the first arm 20 inserted into the patient. The arm 20 is inserted with a first lateral approach in the direction of arrow S along insertion path 111. The first end 21 is inserted through the interspinous space 102 and positioned on a first lateral side of the spine. The second end remains on the second lateral side of the spinous processes 103. In one embodiment, the first connector 25 is positioned within the interspinous space 102. Other embodiments may include an insertion amount such that the first connector 25 is either on the first or second lateral side of the spine.

The securing member 40 is attached within the aperture 26 of the first arm 20. The head 41 of the securing member 40 faces outward and is accessible along the insertion path for tightening to securing the orientation of the implant 10 as will be explained below.

Figure 7:
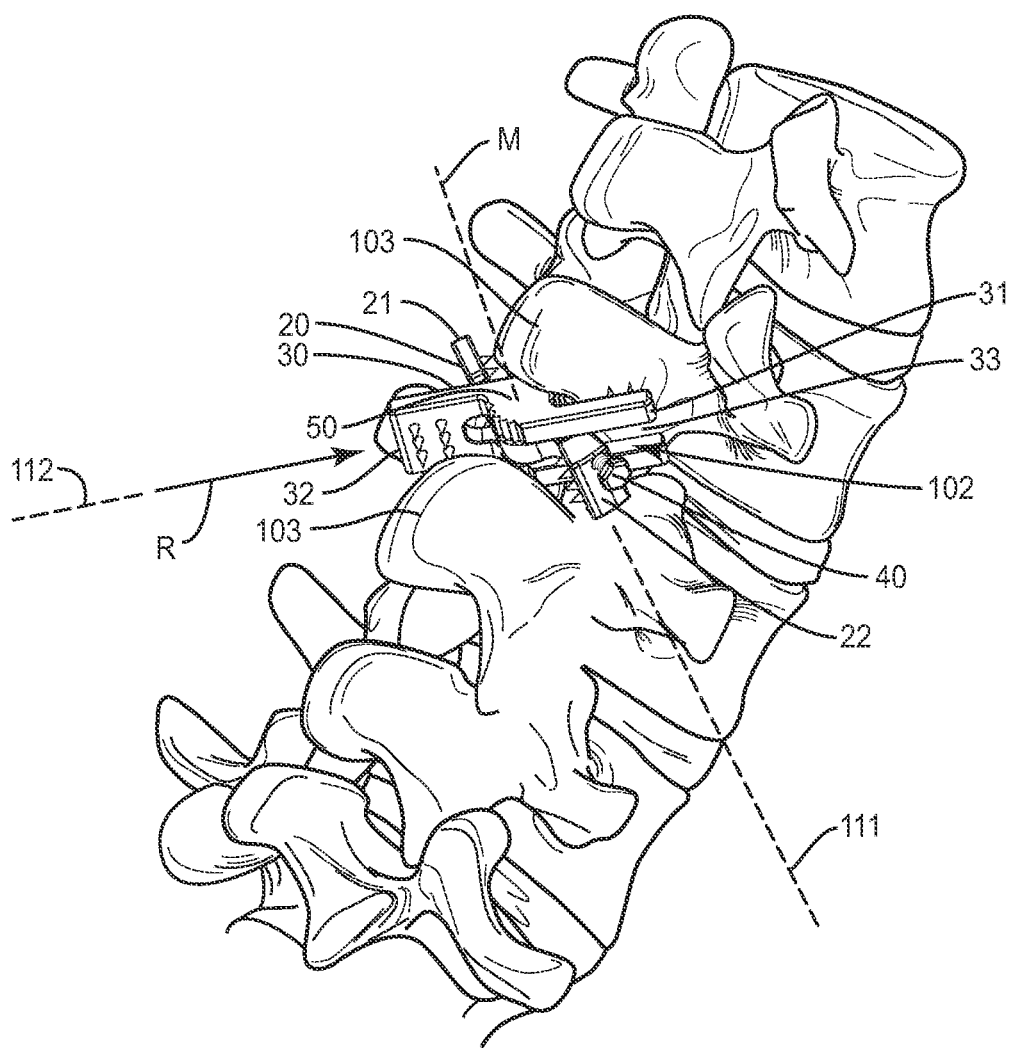

FIG. 7 illustrates the insertion of the second arm 30 into the patient. The arm 30 is inserted with a second lateral approach in the direction of arrow R along the second insertion path 112. In one embodiment, the first and second insertion paths are offset by about 90°.

During insertion, the second arm 30 is aligned to extend around the first arm 20 with the intermediate section 24 positioned within the gap 33. This positions the fingers 34, 35 on opposing sides of the first arm 20. The second arm 30 is moved further relative to the first arm 20 with second arm 20 moving inward along the gap 33. During the movement, the first connector 25 on the first arm 20 is aligned with the second connector 60 on the second arm 30.

In one embodiment, the first connector 25 includes first and second sections 25a, 25b on opposing sides of the intermediate section 24. The second connector 60 also includes first and second sections 60a, 60b on opposing inner surfaces 36 of the fingers 34, 35. During relative movement of the arms 20, 30, the first section 25a is aligned with the first section 60a, and the second section 25b is aligned with the second section 60b. Further relative movement of the arms causes the first section 25a to enter the first channel 61a and the second section 25b to enter the second channel 61b. Additional movement moves the sections 25a, 25b along the respective channels 61 until the sections 25a, 25b enter into the respective sockets 62. The additional depth of the sockets 62 relative to the channels 61a, 61b maintains the positioning of the sections 25a, 25b and the connection of the first and second arms 20, 30.

The combination of the first and second connectors 25, 60 forms a ball joint 50 that connects the first and second arms 20, 30. The rounded shapes of the corresponding sections 25a, 25b and sockets 62 provides for pivoting movement of the arms 20, 30 about a pivot axis M that extends through the joint 50. Each of the sections 25a, 25b and sockets 62 are positioned along the pivot axis M.

In one embodiment, the movement of the sections 25a, 25b along the channels 61a, 61b and into the sockets 62 provides tactile feedback to the surgeon. This feedback may provide for the surgeon to "feel" the relative position between the arms 20, 30. Further imaging systems may be used during the method to enable the surgeon to visually determine the relative positions of the arms 20, 30, and the positions relative to the vertebral members 100.

In one embodiment, the method includes the second arm 30 sliding over the first arm 20 (i.e., the first arm 20 remains relatively stationary in the patient). Other embodiments may include movement of just the first arm 20, or movement of both arms 20, 30.

As illustrated in FIG. 7, the arms 20, 30 may be in an open orientation at the time the joint 50 is formed with the first ends 21, 31 spaced a distance apart and the second ends 22, 32 also being spaced apart. This open orientation may position the arms 20, 30 away from the spinous processes 103.

Figure 8:
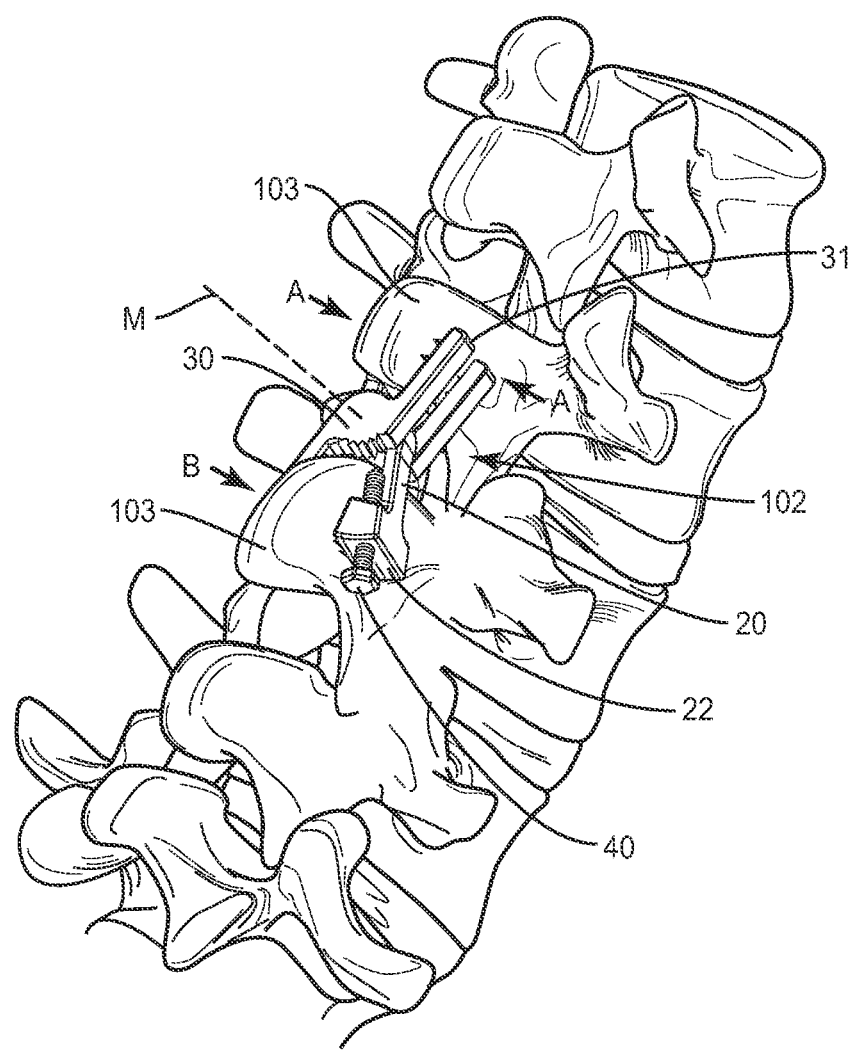

Once the arms 20, 30 are connected together to form the joint 50, the arms 20, 30 may be pivoted about the joint M as illustrated in FIG. 8. This movement causes the inner lateral sides of the first ends 21, 31 to move together as indicated by arrows A and contact against the opposing lateral sides of a first spinous process 103. This movement also causes the inner lateral sides of the second ends 22, 32 to move together and contact against the opposing lateral sides of the second spinous process 103. The teeth 27, 37 that extend outward from the arms 20, 30 engage with the spinous processes 103. In one embodiment, the insertion instruments 110 remain connected to the arms 20, 30 and provide the force for pivoting the arms 20, 30.

Figure 9:
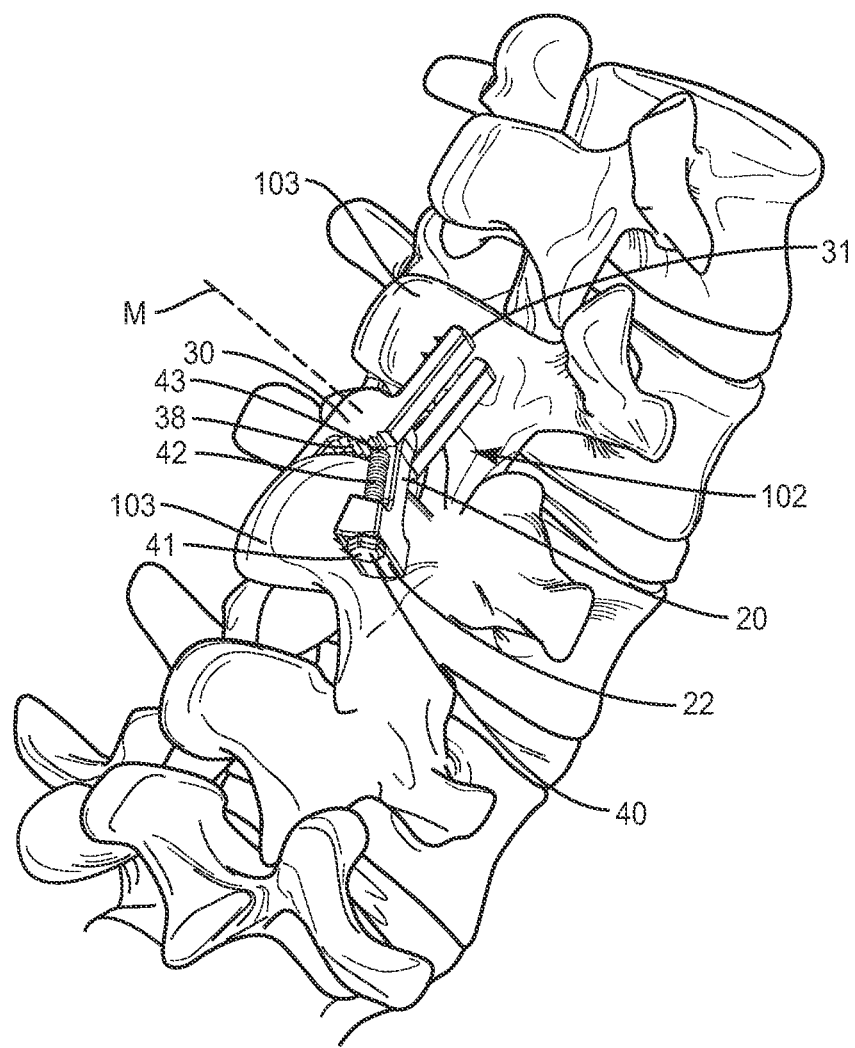

Once the arms 20, 30 are in the desired orientation, the securing member 40 is engaged to maintain the position. As illustrated in FIG. 9, the securing member 40 extends through the aperture 26 in the first arm 20. The member 40 is rotated with a tip 43 moved into contact against the ribs 38 on the second arm 30. This contact prevents additional movement of the arms 20, 30 and maintains the orientation.

The securing member 40 is aligned with the first arm 20 with the head 41 accessible to the surgeon. This provides for the surgeon to apply a force to the head 41 to rotate the member 40 and secure the orientation. The surgeon is able to use the same insertion path 111 used during insertion of the first arm 20 to access and tighten the member 40.

FIG. 9 includes an embodiment with a single securing member 40. Other embodiments may include two or more securing members 40 that engage both arms 20, 30 to maintain the position. In one embodiment, a second securing member 40 extends through a second aperture at the end of the second arm and contacts against the second arm 30.

Figure 10:
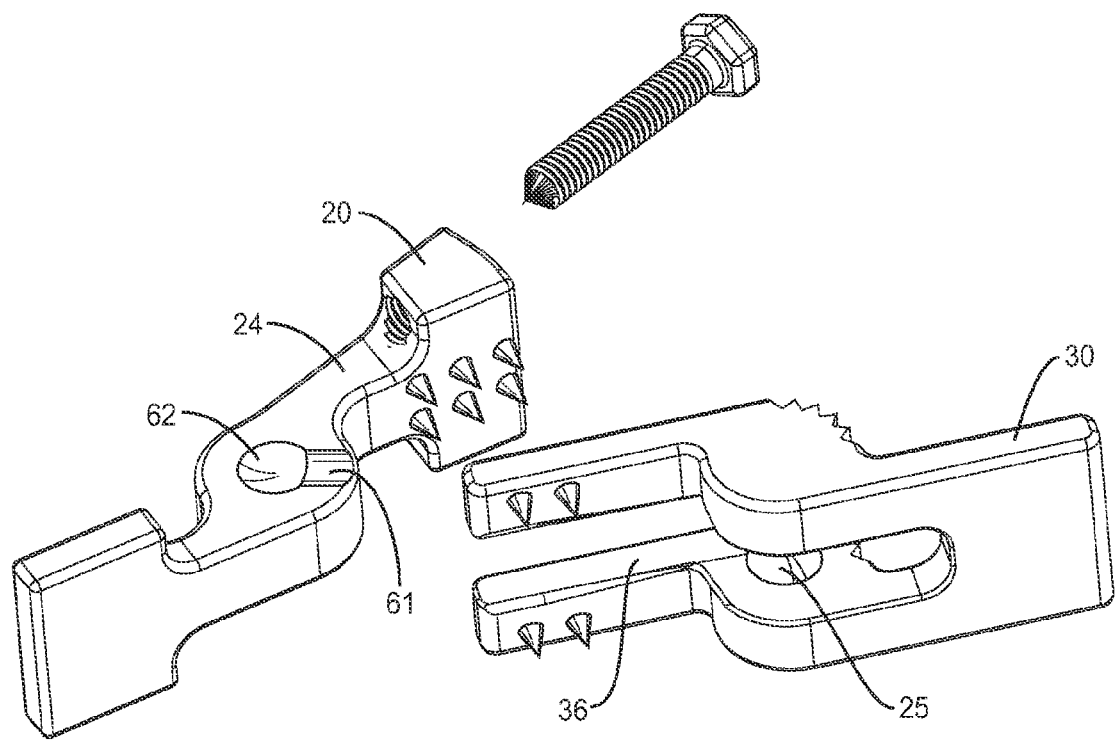
FIG. 10 is an exploded perspective view of an implant.

The embodiment disclosed above includes the first arm 20 with a first connector 25 with one or more sections that extends outward from the intermediate section 24, and the second arm 30 with a second connector 60 with on or more channels 61 and sockets 62 that extend into the inner surfaces 36. The implant 10 may also include various other configurations. FIG. 10 includes an embodiment with the first arm 20 with a pair of sockets 62 and channels 61 that extend into the intermediate section 24, and the second arm 30 with a pair of extensions 25 that extend outward from the inner surfaces 36. The arms 20, engage together in a similar manner described above to form a ball joint for a pivoting implant 10.

Figure 11:
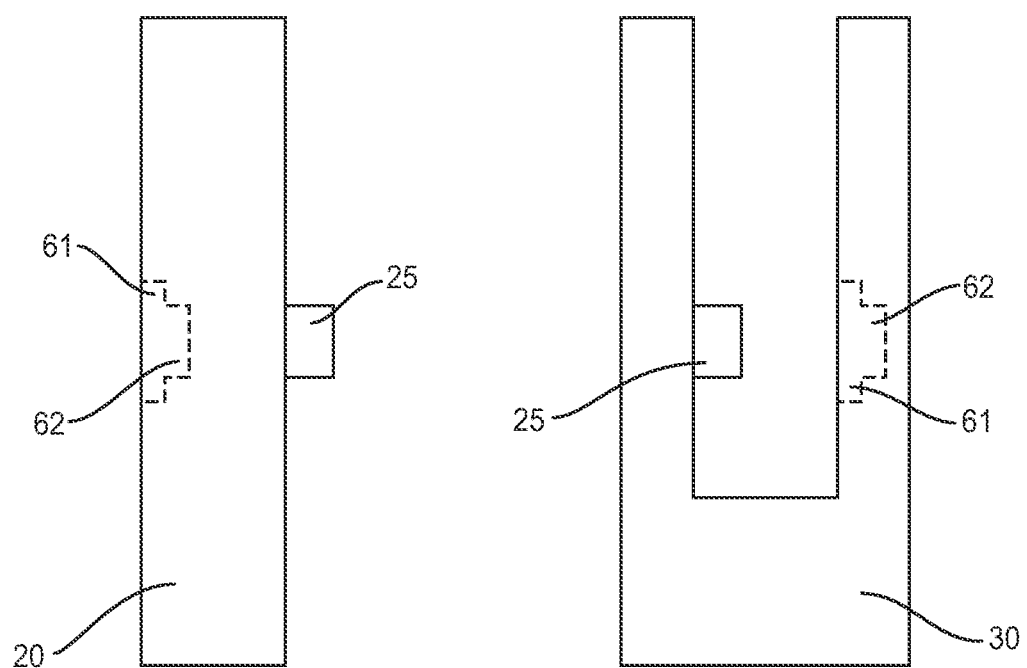
FIG. 11 is a schematic view of an implant with first and second arms.

FIG. 11 schematically illustrates an implant with first and second arms 20, 30. Each of the arms 20, 30 includes a first extension 25 that extends outward from one of the surfaces, and a channel 61 and socket 62 that extend into one of the surfaces. The arms 20, 30 engage together with the extension 25 of the first arm 20 engaged with the socket 62 of the second arm, and the extension 25 of the second arm 30 engaged with the socket 62 of the first arm.

Figure 12:
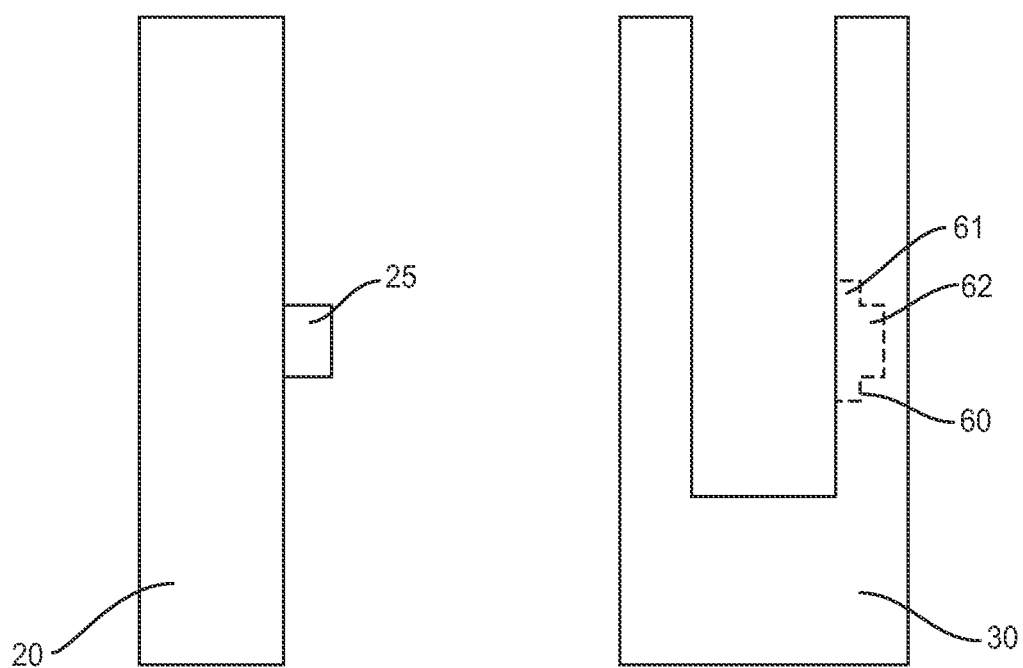
FIG. 12 is a schematic view of an implant with first and second arms.

In some embodiments, one or both arms 20, 30 may include a single connector. FIG. 12 includes an embodiment with the first arm 20 include a first connector 25 including a single extension, and the second arm 30 including a second connector 60 with a single channel 61/socket 62. Other embodiments include the arms 20, 30 with different numbers of connectors (e.g., first arm 20 with a single extension 25 and second arm 30 with two channels 61/sockets 62).

The arms 20, 30 may be constructed from a variety of materials, including but not limited to titanium and its alloys, stainless steel, and cobalt chrome. The material may allow for deformation of the first connector 25 and/or the fingers 34, 35 when the first arm 20 and second arm 30 are connected together. The deformation may occur as the first connector 25 moves along the one or more channels 61 and into the one or more sockets 62.

The implant 10 may be used in various regions of the spine. In one embodiment, the implant 10 is inserted within the lumbar region of the spine. Other embodiments may include insertion of the implant 10 along the cervical or thoracic regions.

The various implants may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A spinal implant comprising:
    a first arm having opposing first and second ends;
    a second arm having first and second ends, the second arm positioned across the first arm; and
    a ball joint positioned along intermediate sections of the arms and formed by first and second extensions on opposing sides of one of the first and second arms positioned respectively in first and second sockets defined by first and second inner surfaces of the other arm, the first and second inner surfaces being spaced apart from one another, one of the first and second arms including a gap formed between opposing fingers that extends inward from a first end of the arm to at least the ball joint with the other arm positioned within the gap;
    the first and second arms pivotal about the ball joint between first and second orientations with the first ends of each of the arms and the second ends of each of the arms positioned a greater distance apart in the first orientation than in the second orientation.

2. The spinal implant of claim 1, further comprising a first channel that extends from an outer edge of the first arm to the first socket and a second channel that extends from the outer edge to the second socket, the first channel having a smaller depth than the first socket and the second channel having a smaller depth than the second socket.

3. The spinal implant of claim 1, wherein each of the first and second extensions includes rounded shapes.

4. The spinal implant of claim 1, further comprising a securing member that extends through an aperture in the first arm and contacts against at least one of a plurality of parallel ribs on the second arm, the securing member configured to fix the relative positions of the first and second arms.

5. The spinal implant of claim 1, wherein each of the extensions includes the same shape and size and each of the sockets includes the same shape and size.

6. The spinal implant of claim 1, wherein the opposing sides are planar side surfaces that are spaced apart from one another by a lateral surface that extends perpendicular to each of the planar side surfaces.

7. The spinal implant of claim 1, wherein:
the first arm comprises teeth positioned on a first lateral side of the first arm and on an opposite second lateral side of the first arm;
the second arm comprises teeth positioned on a first lateral side of the second arm and on an opposite second lateral side of the second arm; and
the first lateral sides face away from one another and the second lateral sides face away from one another.

8. A spinal implant comprising:
an elongated first arm with opposing first and second ends, the first arm including a first connector positioned at a midpoint between the ends that includes a first extension that extends outward from a first side of the first arm and a second extension that extends outward from an opposing second side of the first arm; and
an elongated second arm with opposing first and second ends, the second arm including a gap that extends inward from the first end towards the second end and first and second fingers on opposing sides of the gap that each include an inner side that faces into the gap;
the second arm further including a first channel and first socket in the inner side of the first finger and a second channel and second socket in the inner side of the second finger, the sockets having a greater depth into the inner sides than the channels;
the first and second extensions of the first arm positioned in the sockets of the second arm to connect the first and second arms.

9. The spinal implant of claim 8, wherein the first and second ends of the first arm are wider than the gap.

10. The spinal implant of claim 8, wherein each of the first and second extensions includes a rounded shape and the first and second sockets include a rounded shape.

11. The spinal implant of claim 8, further comprising a securing member that extends through an aperture in one of the first and second arms and contacts against the other of the first and second arms to secure the first and second arms.

12. The spinal implant of claim 8, wherein each of the first and second channels is parallel with the first and second fingers.

13. The spinal implant of claim 8, wherein each of the first and second channels include an opening at the gap with the openings facing in a common direction as the first end of the second arm.

14. The spinal implant of claim 8, wherein the second arm includes a first portion with a length that is substantially straight, a second portion at the second end with a length that is substantially straight, and an intermediate transverse portion that extends between the first and second portions, the first and second channels positioned at the intermediate transverse portion and facing towards the first end of the second arm.

15. The spinal implant of claim 8, wherein at least one of the channels includes a tapered shape that is wider at an outer edge away from the socket and narrower at an inner edge at the socket.

16. A method of inserting an implant into an interspinous space formed between first and second spinous processes, the method comprising:
providing the spinal implant of claim 8;
inserting from a first lateral side the first arm into the patient;
positioning the first end of the first arm on a second lateral side of the first spinous process and the second end of the first arm on a first lateral side of the second spinous process;
inserting from a second lateral side the second arm into the patient;
positioning the second arm across the first arm with the first end of the second arm on a first lateral side of the first spinous process and the second end of the second arm on a second lateral side of the second spinous process;
inserting the extensions of the first arm into the channels of the second arm; and
moving the extensions along the channels and into the sockets.

17. The method of claim 16, further comprising pivoting the first and second arms about an axis that extends through the extensions and the sockets and adjusting a distance between the first ends and the second ends of the first and second arms.

18. The method of claim 16, further comprising inserting the first arm into the gap in the second arm.

19. The method of claim 16, wherein the first arm is inserted into the patient before the second arm.

20. A spinal implant comprising:
a first arm having opposing first and second ends;
a second arm having first and second ends, the second arm positioned across the first arm; and
a ball joint positioned along intermediate sections of the arms and formed by first and second extensions on opposing sides of one of the first and second arms positioned respectively in first and second sockets defined by first and second inner surfaces of the other arm, the first and second inner surfaces being spaced apart from one another, the opposing sides being planar side surfaces that are spaced apart from one another by a lateral surface that extends perpendicular to each of the planar side surfaces;
the first and second arms pivotal about the ball joint between first and second orientations with the first ends of each of the arms and the second ends of each of the arms positioned a greater distance apart in the first orientation than in the second orientation.

* * * * *